United States Patent [19]

Sprague

[11] Patent Number: Plant 7,337

[45] Date of Patent: Sep. 25, 1990

[54] *PRUNUS PERSICA* SPRAGUE PEACH BUSH

[76] Inventor: James W. Sprague, 1605 S. Mountain Ave., Apt. 5, Ontario, Calif. 91761

[21] Appl. No.: 484,839

[22] Filed: Feb. 26, 1990

[51] Int. Cl.[5] ..... A01H 5/00

[52] U.S. Cl. ..... Plt./43

[58] Field of Search ..... Plt./34

[56] References Cited

U.S. PATENT DOCUMENTS

P.P. 6,119 3/1988 Sprague ..... Plt. 43

*Primary Examiner*—James R. Feyrer

*Attorney, Agent, or Firm*—Denton L. Anderson

[57] ABSTRACT

A new and distinct variety of *Prunus persica* characterized by the short, bushy shape of its trees and by the firmness and apparent virus-free nature of its fruit.

4 Drawing Sheets

1

BACKGROUND

The present invention relates to a new and distinct variety of *Prunus persica,* the novel characteristics of which reside particularly in the short, bushy shape of the tree.

The new Prunus was first discovered by James W. Sprague in 1984. It originated from a sport branch on a *Prunus persica* tree of the Last Chance Peach Number One variety, grown in a cultivated orchard in the West Antelope Valley of Lancaster, Calif. Thereafter, the new variety was successfully asexually reproduced by Mr. Sprague by budding from the sport onto root stock of the Last Chance Peach Number One variety and other *Prunus persica* varieties. Such asexual reproduction resulted in several progeny trees which have consistently displayed the short, bushy tree shape, firm fruit, virus-free fruit and apparent high temperature dormancy characteristics found on the parent sport branch.

An interesting characteristic of the new variety is its short, bushy tree shape. Mature trees naturally assume this shape without pruning. The tree grown largely without horizontal branches. No branches are thicker than about 1⅛ inch in diameter and most of the branches are much thinner than that. The "trunk" is generally less than eight inches in height. The trees rarely grow taller than about four and one-half to five feet in height.

Another interesting characteristic of the new variety is the virtually virus-free character of the fruit. Thus, the fruit can be frozen for long periods of time without discoloring and without additives.

Another interesting characteristic of the new variety is the firmness of the fruit which allows the fruit to be transported and stored with minimal damage.

Another interesting characteristic of the new variety is the wiry nature of the branches and the tendency of the branches to bend but not break under the weight of maturing fruit so that fruit-laden branches arch over until fruit growing at the further-most end rests upon the ground.

These characteristics make the new variety distinct from known varieties of *Prunus persica.*

In particular, the new variety is distinct from the *Prunus persica* Last Chance Peach Number One Variety in several characteristics as set forth in Table I.

2

TABLE I

| Characteristic | Prunus Persica Last Chance Peach Number One | Prunus Persica Sprague Peach Bush |
|---|---|---|
| Shape of tree | Dwarf tree | Bush |
| Height of tree at maturity | 7–9 feet | 4½–5 feet |
| Height of tree "trunk" | 1½–4 feet | 1–8 inches |
| Average thickness of primary branches | 2 inches | ¾ inches |
| Length of leaf | 4–4½ inches | 4½–5 inches |
| Distribution of fruit | Mostly in lower ⅔ of tree | Uniform throughout |
| Maturation of tree | First sizeable fruit crop in third year | First sizeable fruit crop in second year |
| Size of fruit | Vertical diameter: 2¾–3¼ inches Horizontal diameter: 2¼–3 inches | Vertical diameter: 2½–3 inches Horizontal diameter: 2–2¾ inches |
| Shape of fruit | Upper half slightly asymmetrical | Symmetrical |
| Exterior color of fruit | Yellow color | Pale yellow color especially on interior of bush |

The new variety is also distinct from the *Prunus persica* Last Chance Peach Number One variety in that the bloom time of the new variety is slightly longer by about one week and the fruit of the new variety appears slightly earlier but takes slightly longer to mature.

Other distinctive characteristics of the new variety are exemplified in the accompanying illustrations, wherein.

TECHNICAL DESCRIPTION

Figure 1:
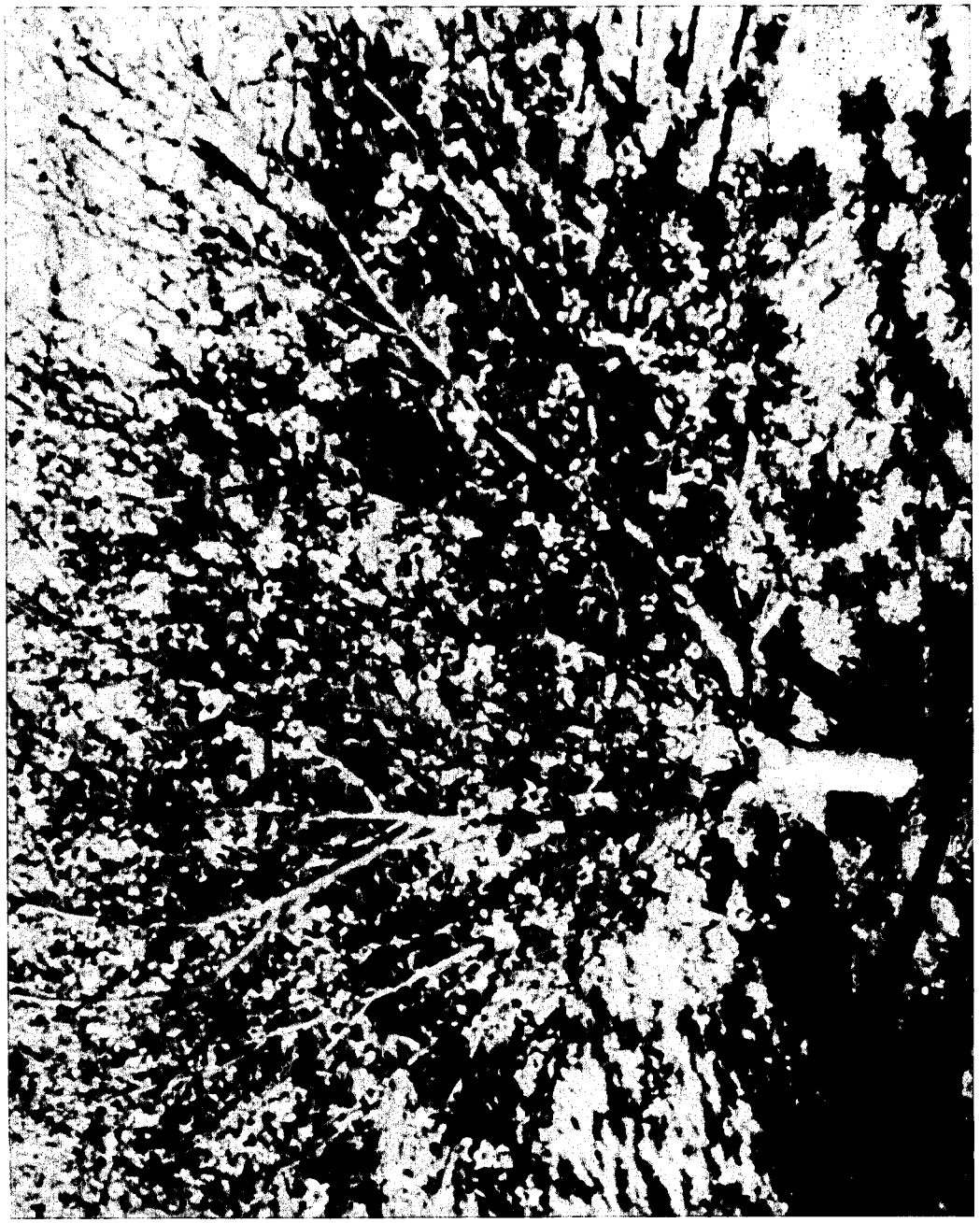
FIG. 1 shows an adult parent tree.
Figure 2:
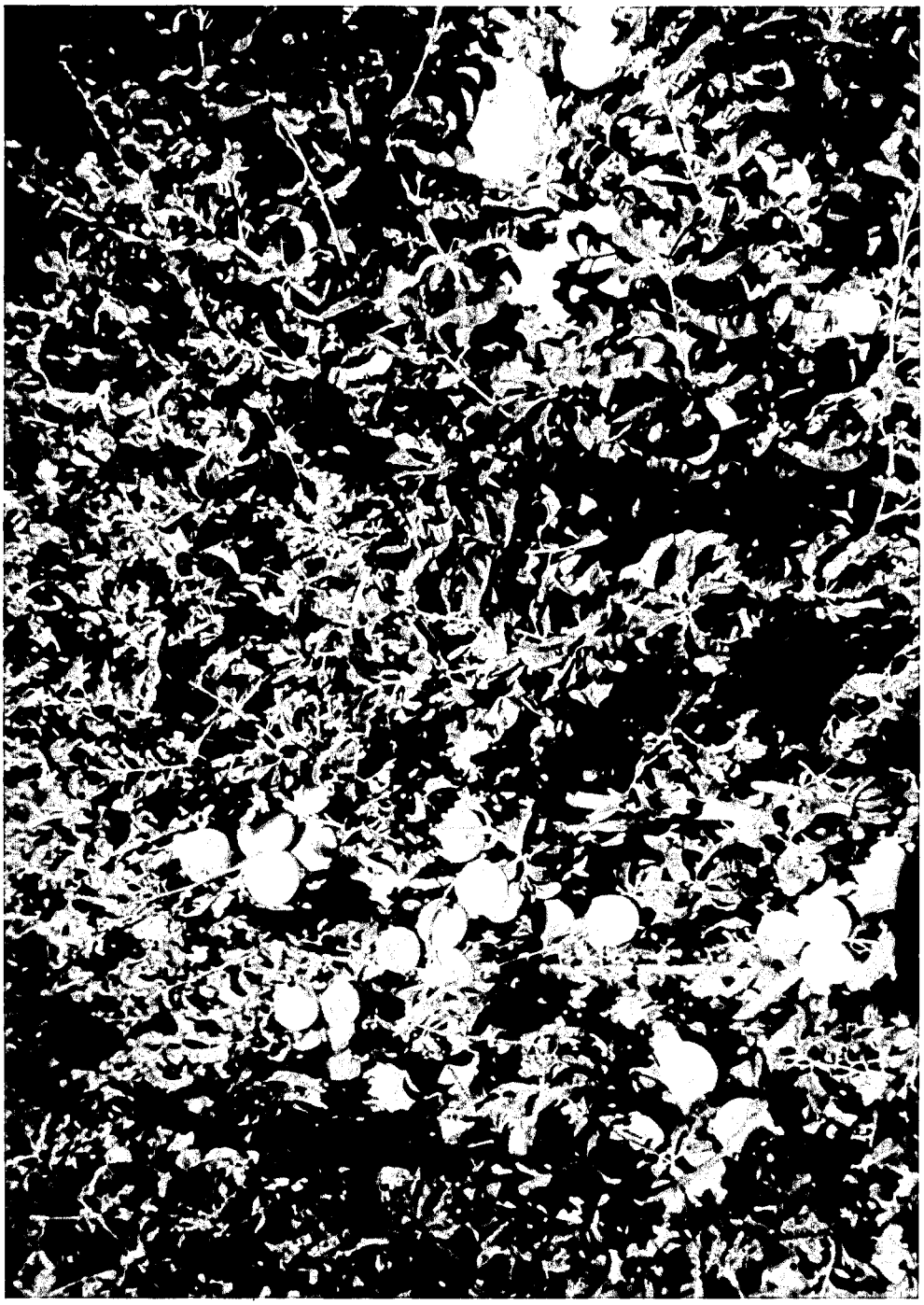
FIG. 2 is a close up of a branch with adult leaves.
Figure 3:
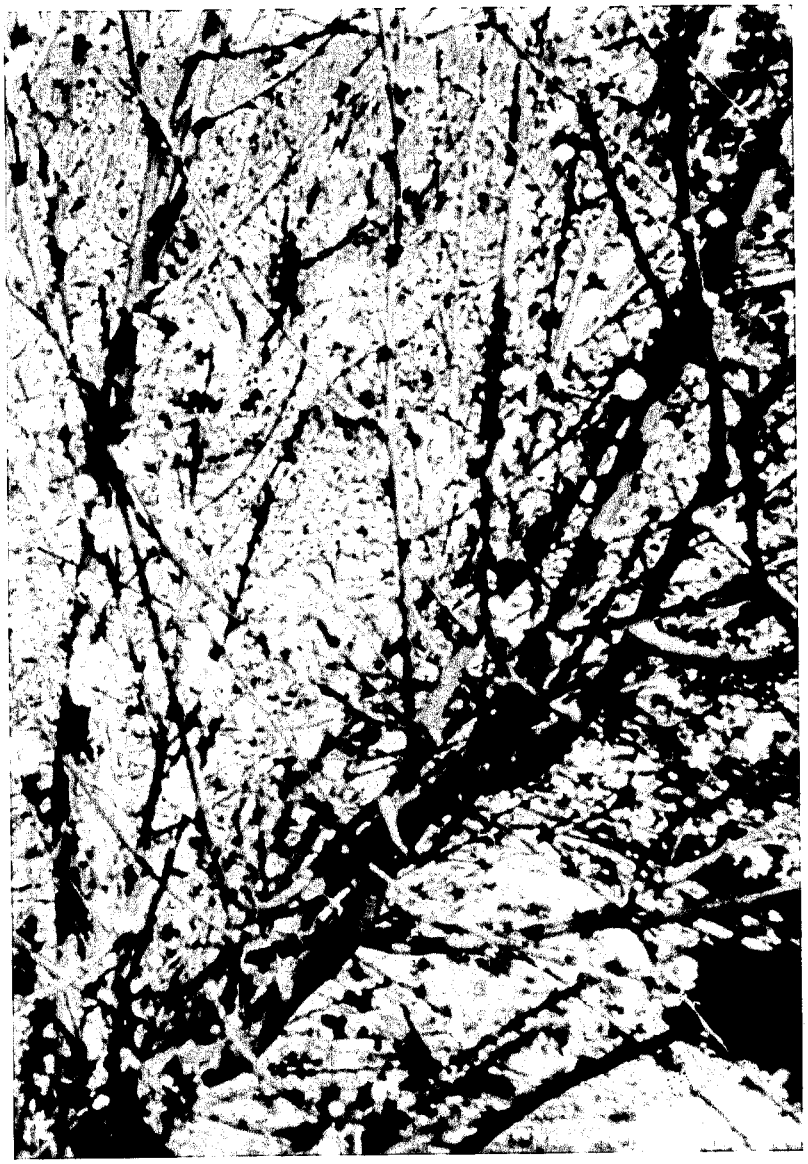
FIG. 3 is a close up of a branch with adult inflorescence.
Figure 4:
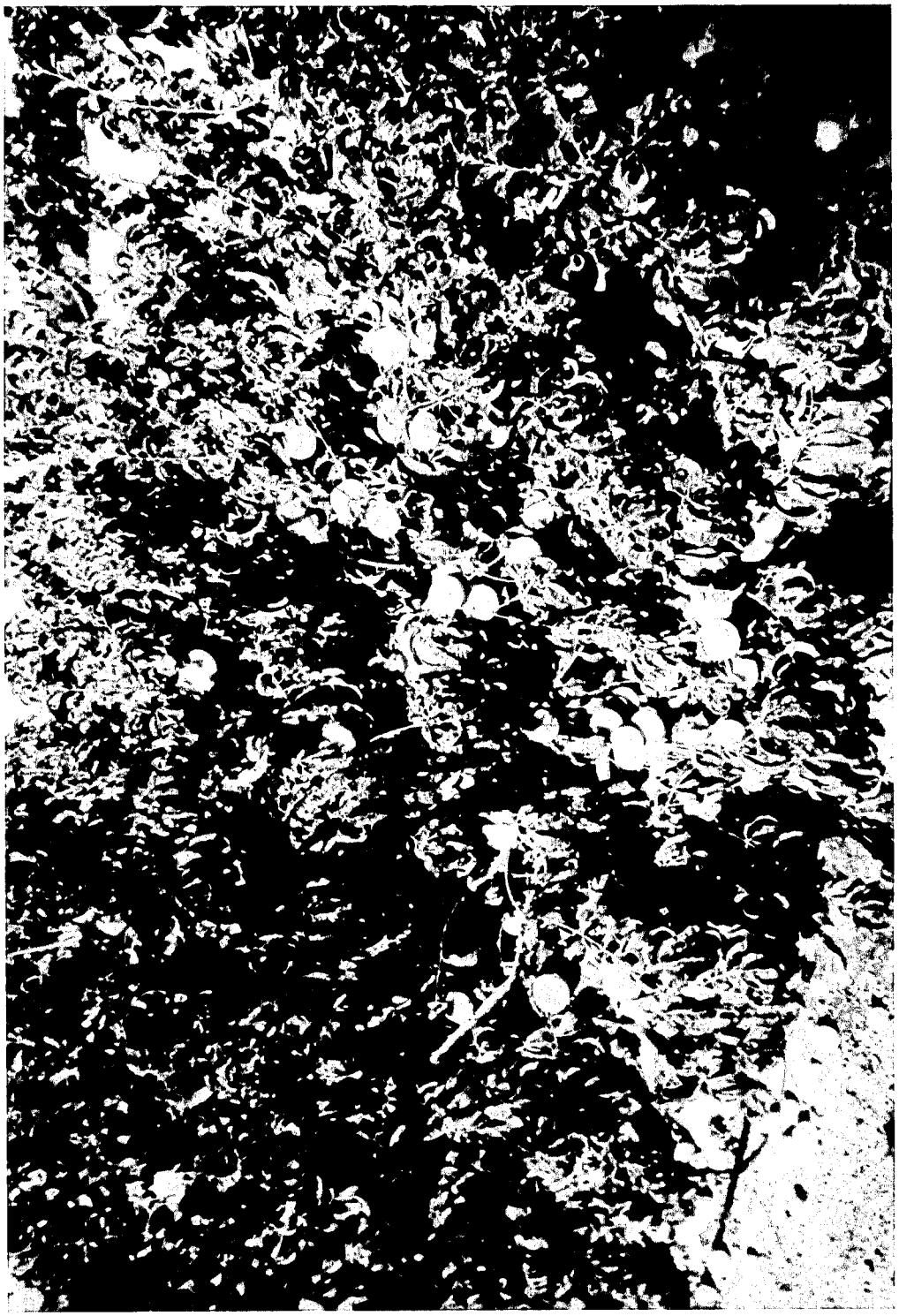
FIG. 4 is a close up of a branch bearing ripened fruit.

The following is a description in some detail of the new variety of *Prunus persica.*

Tree: Short, bushy shape, characterized by few horizontal branches.

About four and one-half to five feet tall at maturity. Water frugal, very dense, very rigorous, regular bearer, very productive. Dormancy period apparently induced by temperatures considerably higher than normal dormancy-inducing temperatures. Bears fruit in October until as late as about the first week in November.

Foliage:

*Leaves.*—Obovate, spatulate, acutely pointed, medium thickness, dark green color, smooth texture, four and one-half to about five inches in length and one and one-half inches in width. Glandular and finely serrate margin. Petiole of medium length and medium thickness, stipules at base, average of eighteen to twenty glands per leaf, opposite and positioned along full length of leaf, globose to reinform, normal green color.

*Branches.*—All vertical, few horizontals. Thickness no greater than about one and one-eighth inch in diameter. Smooth texture, red to brown in color, glossy appearance, lenticels medium in number.

Flower: Pink color, influorescent from February 25 through March 31st.

*Buds.*—Hardy, plump, medium length and somewhat appressed.

Fruit:

*Form.*—Uniform shape, shallow inconspicuous suture, circular cavity with suture showing on one side, slightly to strongly rounded ventral surface, rounded basis, short apex, 2½–3 inch vertical diameter and 2–2¾ inch horizontal diameter.

*Skin.*—Medium thickness, not tough or tender, tenacious to flesh, less than usual down that does not roll up when rubbed. Fifty to seventy percent red in color.

*Flesh.*—Yellow color, red color on surface of cavity, abundant amygdalin, moderate juice, very firm texture, austere flavor, distinct aroma, excellent eating quality, apparently virus-free. Retains color, texture and flavor upon freezing and thawing.

*Fibres.*—Fine, tender, few in number.

*Stone.*—Free, parts from flesh smoothly, short fibres, oblong to oval shape, oblique base, broad helum, rounded apex, regularly furrowed toward apex, pitted throughout, rounded ridges, elongated pits, thick ventral edge, narrow dorsal edge, continuous ridges on either side, brownish-red color, about one-inch length and about three-quarter inch in diameter.

The principal novel characteristics of the new variety of *Prunus persica* is its short, bushy shape. This allows its fruit to be easily harvested without the aid of ladders. Together with the wiry strength of its branches, the short bushy shape of the new variety makes the new variety highly resistant to wind damage when laden with fruit. Branches laden with fruit bend downwardly but do not break. Low, fruit laden branches become supported by the ground. The overall effect is a marked reduction of "whipping action" induced by gusts of wind and a resultant minimization of wind-induced damage.

Another novel characteristic of the new variety of *Prunus persica* is the substantially virus-free nature of the fruit. This allows the fruit to be stored for long periods with minimal decay. Also, the fruit can be frozen and the flesh will not darken.

The new variety of *Prunus persica* is further characterized by the firm flesh of the fruit. This allows the fruit to be transported and stored with minimal damage.

What is claimed is:

1. A new and distinct variety of *Prunus persica* as described and shown herein characterized particularly by the short, bushy shape of its trees and by the firmness and substantially virus-free nature of its fruit.

* * * * *